United States Patent
Stookey et al.

(10) Patent No.: US 7,270,543 B2
(45) Date of Patent: Sep. 18, 2007

(54) HANDPIECE FOR CARIES DETECTION

(75) Inventors: George Kenneth Stookey, Noblesville, IN (US); Kenneth Robert Dunipace, Indianapolis, IN (US); Bryan Ellis Blackwell, Brownsburg, IN (US); Masatoshi Ando, Indianapolis, IN (US)

(73) Assignee: Therametric Technologies, Inc., Indianapolis, IN (US)

( * ) Notice: Subject to any disclaimer, the term of this patent is extended or adjusted under 35 U.S.C. 154(b) by 250 days.

(21) Appl. No.: 10/879,407

(22) Filed: Jun. 29, 2004

(65) Prior Publication Data

US 2005/0287490 A1    Dec. 29, 2005

(51) Int. Cl.
*A61C 5/00*    (2006.01)
*A61C 3/00*    (2006.01)

(52) U.S. Cl. ......................... 433/215; 433/29
(58) Field of Classification Search ............ 433/29–31, 433/80, 215
See application file for complete search history.

(56) References Cited

U.S. PATENT DOCUMENTS

| | | | | |
|---|---|---|---|---|
| 4,215,698 A | * | 8/1980 | Nuwayser | .................. 600/547 |
| 4,290,433 A | | 9/1981 | Alfano | |
| 4,479,499 A | | 10/1984 | Alfano | |
| 4,515,476 A | * | 5/1985 | Ingmar | ....................... 356/318 |
| 4,790,751 A | * | 12/1988 | Reinhardt et al. | ............. 433/29 |
| 4,976,951 A | | 12/1990 | Rosenberg et al. | |
| 5,061,880 A | | 10/1991 | Hashiguchi et al. | |
| 5,280,278 A | | 1/1994 | Vick | |
| 5,306,144 A | * | 4/1994 | Hibst et al. | ................... 433/29 |
| 5,382,163 A | | 1/1995 | Putnam | |
| 5,503,559 A | | 4/1996 | Vari | |
| 5,550,380 A | | 8/1996 | Sugawara et al. | |
| 5,570,182 A | | 10/1996 | Nathel et al. | |
| 5,742,700 A | | 4/1998 | Yoon et al. | |
| 5,759,030 A | | 6/1998 | Jung et al. | |
| 5,818,587 A | | 10/1998 | Devaraj et al. | |
| 5,894,620 A | | 4/1999 | Polaert et al. | |
| 5,961,327 A | | 10/1999 | Löhn | |
| 6,008,889 A | | 12/1999 | Zeng et al. | |
| 6,024,562 A | | 2/2000 | Hibst et al. | |
| 6,053,731 A | | 4/2000 | Heckenberger | |
| 6,074,616 A | | 6/2000 | Buechler et al. | |
| 6,102,704 A | | 8/2000 | Eibofner et al. | |
| 6,135,774 A | | 10/2000 | Hack et al. | |
| 6,186,780 B1 | * | 2/2001 | Hibst et al. | ................... 433/29 |
| 6,201,880 B1 | * | 3/2001 | Elbaum et al. | ............. 382/100 |
| 6,231,338 B1 | | 5/2001 | de Josselin de Jong et al. | |
| 6,309,835 B1 | | 10/2001 | Iyer et al. | |

(Continued)

FOREIGN PATENT DOCUMENTS

DE        40 09 438        9/1991

(Continued)

OTHER PUBLICATIONS

Web pages (3), www.kavousa.com, DIAGNOdent, Kavo Diagno Dent, dated Mar. 10, 2001.

(Continued)

*Primary Examiner*—John J Wilson
(74) *Attorney, Agent, or Firm*—Baker & Daniels LLP

(57) ABSTRACT

A dental implement is provided including a housing, a light source, a light detecting device, and a translucent member.

2 Claims, 4 Drawing Sheets

U.S. PATENT DOCUMENTS

| | | | |
|---|---|---|---|
| 6,393,315 | B1 | 5/2002 | Aprahamian et al. |
| 6,485,300 | B1 | 11/2002 | Muller et al. |
| 6,512,855 | B1 | 1/2003 | Delean |
| 6,522,147 | B1 | 2/2003 | Pickard et al. |
| 6,533,434 | B2 | 3/2003 | Yuen |
| 6,561,802 | B2* | 5/2003 | Alexander ................... 433/29 |
| 6,584,341 | B1* | 6/2003 | Mandelis et al. ........... 600/476 |
| 6,592,371 | B2 | 7/2003 | Durbin et al. |
| 6,724,522 | B2 | 4/2004 | Hartung |
| 6,764,309 | B2* | 7/2004 | Cozean et al. ............... 433/215 |
| 6,769,911 | B2* | 8/2004 | Buchalla et al. ............... 433/29 |
| 6,918,762 | B2* | 7/2005 | Gill et al. ...................... 433/29 |
| 2002/0119100 | A1* | 8/2002 | Okada et al. ................. 424/9.7 |
| 2003/0022126 | A1* | 1/2003 | Buchalla et al. ............... 433/29 |
| 2003/0097122 | A1 | 5/2003 | Ganz et al. |
| 2003/0113823 | A1 | 6/2003 | Gregory |
| 2003/0122771 | A1 | 7/2003 | Sumiyoshi et al. |
| 2003/0156788 | A1 | 8/2003 | Henning |
| 2004/0023184 | A1 | 2/2004 | de Josselin de Jong et al. |
| 2004/0038169 | A1 | 2/2004 | Mandelkern et al. |
| 2004/0202356 | A1 | 10/2004 | Stookey et al. |
| 2004/0236232 | A1 | 11/2004 | Jonusauskas et al. |
| 2004/0240716 | A1 | 12/2004 | de Josselin de Jong et al. |
| 2005/0003323 | A1 | 1/2005 | Katsuda et al. |

FOREIGN PATENT DOCUMENTS

| | | |
|---|---|---|
| EP | 0 113 152 A2 | 7/1984 |
| EP | 0 326 497 A2 | 8/1989 |
| EP | 0 792 618 A1 | 9/1997 |
| EP | 0 920 831 A1 | 6/1999 |
| EP | 1 269 909 A1 | 1/2003 |
| JP | 2004/089238 A | 3/2004 |
| JP | 2004/163131 A | 6/2004 |
| WO | WO 92/06671 A1 | 4/1994 |
| WO | WO 96/12291 A1 | 4/1996 |
| WO | WO 00/64242 A1 | 11/2000 |
| WO | WO 00/67635 | 11/2000 |
| WO | WO 01/02839 A1 | 1/2001 |
| WO | WO 2004/89197 A1 | 10/2004 |

OTHER PUBLICATIONS

Brochure, "Sophistication. Simplified. The A-Dec Intraoral Camera", 2 pgs. (2003).

Al-Khateeb et al., "A Longitudinal Laser Fluorescence Study of White Spot Lesions in Orthodontic Patients," American Journal of Orthodontics and Dentofacial Orthopedics, vol. 113, No. 6, pp. 595-602 (Jun. 1998).

Al-Khateeb et al., "Light-Induced Fluorescence Studies on Dehydration of Incipient Enamel Lesions," Caries Research, vol. 36, pp. 25-30 (2002).

Al-Khateeb et al., "Light-Induced Fluorescence Studies on Dehydration of Incipient Enamel Lesions—Clinical Considerations," Caries Res., vol. 32, p. 285 (Abst #53) (1998).

Ando et al., "Comparative Study To Quantify Demineralized Enamel in Deciduous and Permanent Teeth Using Laser-And Light-Induced Fluorescence Techniques", Caries Res, vol. 35, pp. 464-470 (2001a).

Ando, et al., "Effect of Dehydration on White-Spot Quantification with QLF in Vitro", J. Dent. Res., vol. 80; p. 718 (Abst #1536) (2001b).

Ando, et al., "Pattern of Fluorescence Intensity During Dehydration as Determined by Quantitative Light-Induced Fluorescence in Vitro", Caries Res., vol. 35, p. 270 (Abst #16) (2001c).

Angmar-Mansson, et al., "Quantitative Light-Induced Fluorescence (QLF): a method for assessment of incipient caries lesions", Dentomaxillofacial Radiology, No. 30, pp. 298-307 (2001).

Banerjee, et al., "Autofluorescence and Mineral Content of Carious Dentine: Scanning Optical and Backscattered Electron Microscopic Studies", Caries Research, vol. 32, pp. 219-226 (1998).

Banerjee, et al., "Dentine Caries Excavation: a review of current clinical techniques", British Dental J., vol. 188, No. 9 (May 13, 2000).

Banerjee, et al., "In vitro Evaluation of Five Alternative Methods of Carious Dentine Excavation", Caries Research vol. 34, pp. 144-150 (2000).

Fisher, et al., "Tooth-Caries Early Diagnosis and Mapping by Fourier Transform Spectral Imaging Fluorescence", Instrumentation Science & Technology, vol. 30(2), pp. 225-232 (2002).

Foreman, "Fluorescent Microstructure of Mineralized Dental Tissues", Intl. Endodontic Journal, vol. 21, pp. 251-256 (1988).

Mujat et al., "The Influence of Drying on Quantitative Laser Fluorescense and Optical Pathlengths in Incipient Natural Caries Lesions," Caries Research, vol. 38, pp. 484-492 (2004).

Pretty, et al., "Detection of in vitro demineralization of primary teeth using quantitative light-induced fluorescence (QLF)", Intl. Journal of Paediatric Dentistry, vol. 12, pp. 158-167 (2002).

Pretty et al., "The Effect of Dehydration on Quantitative Light-Induced Fluorescence Analysis of Early Enamel Demineralization," Journal of Oral Rehabilitation, vol. 31, pp. 179-184 (2004).

Shi et al., "Comparison of QLF and DIAGNOdent for Quantification of Smooth Surface Caries", Caries Research, No. 35, pp. 21-26 (2001).

Spitzer, et al., "The Total Luminescence of Bovine and Human Dental Enamel", Calcif. Tiss. Res., No. 20, pp. 201-208 (1976).

Stookey, "Optical Methods—Quantitative Light Fluorescence," J. Dent. Res., vol. 83(Spec ISS C) (2004).

Traneous, et al., "In vivo Repeatability and Reproducibility of the Quantitative Light-Induced Fluorescence Method", Caries Research No. 36, pp. 3-9 (2002).

van der Veen, et al., "Caries Activity Detection by Dehydration with Quantitative Light Fluorescence", report of Indiana Conference 1999 Early Detection of Dental Caries II, pp. 251-259 (1999).

van der Veen, et al., "The Influence of Mineral Loss on the Auto-Fluorescent Behavior of in vitro Demineralised Dentine", Caries Research, vol. 30, pp. 93-99 (1996).

\* cited by examiner

HANDPIECE FOR CARIES DETECTION

BACKGROUND AND SUMMARY OF THE INVENTION

The invention relates to dental devices and more particularly to devices for detection of tooth decay/dental caries.

While there has been a remarkable decline in the prevalence of dental caries (tooth decay) in U.S. children and adults during the past 40 years, dental caries continues to be a major public health problem in select portions of the U.S. population. Dental caries has been identified as the single most common chronic disease of childhood. Despite the strides made in treating and preventing dental caries, significantly more needs to be done to further combat the problem.

Dental caries is a chronic infectious disease and earlier detection would reduce the ravages of the disease. Current caries detection methods (clinical exams, x-rays) are unable to detect the decay process until it has progressed to a point where it is necessary to place a restoration (filling). Since the loss of mineral from the enamel is a chronic process that occurs over a period of months to years, and since very small lesions (i.e., early detection) are completely reversible through the use of fluoride treatments and other preventive measures, the early detection of dental caries allows dental professionals to administer professional treatments to reverse the caries process rather than undertake more costly and less desirable restorative treatments.

According to the present invention, a dental implement is provided including a housing, a light source, a light detecting device, and a translucent member. The translucent member includes an internal reflective surface and the translucent member directs light from the light source and directs light to the light sensing device.

According to another embodiment of the present invention, a dental implement is provided including a housing, a light source, a light sensing device, and a conduit introducing an external compound.

According to still another embodiment of the present invention, a dental implement is provided including a housing, a light source, a light sensing device, and a readily detachable light conductor including a tissue abutment surface.

According to yet another embodiment of the present invention, a dental implement light conductor is provided including: a proximal end including a proximal light transfer plane, a distal end including a distal light transfer plane, a translucent body, and a reflector located near the distal end. The reflector is sized, shaped, and positioned such that light input to the proximal end is output from the distal end and light input to the distal end is output from the proximal end.

According to another embodiment of the present invention, a method of detecting dental caries is provided including the steps of: providing a handpiece, including a light source, a light receiver, and a light conduit; and abutting the light conduit to selected tissue.

According to still another embodiment of the present invention, a method of detecting dental caries is provided that includes the step of providing a light conductor including a proximal end, a distal end, a translucent body positioned between the proximal end and the distal end, and a reflector located internally to the body and near the distal end such that light input to the proximal end is output the distal end and light input the distal end is output the proximal end.

Additional features of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Tooth decay or dental caries result from a de-mineralization of dental tissue. Introduction of light to dental tissue and observance of the fluorescence of the dental tissue allows early detection of dental caries through a process called quantitative light fluorescence (QLF). "QLF" has been trademarked by Inspektor Dental Care (hereinafter "Inspektor"). The use of the term "QLF" herein is meant to denote a quantitative light fluorescence type system, and not the specific system of Inspektor unless specifically stated otherwise. QLF allows earlier detection than a purely visual inspection and does not have the side effects associated with radiographic examinations. Furthermore, QLF provides an objective method of analysis of dental caries by permitting a dentist or other caregiver to quantify the size of lesions as well as monitor changes in the size of lesions over time. A more detailed description of QLF and a method for utilizing QLF is described in U.S. patent application Ser. No. 10/411,625 to Stookey et al. filed Apr. 10, 2003, the disclosure of which is incorporated herein by reference.

Figure 1:
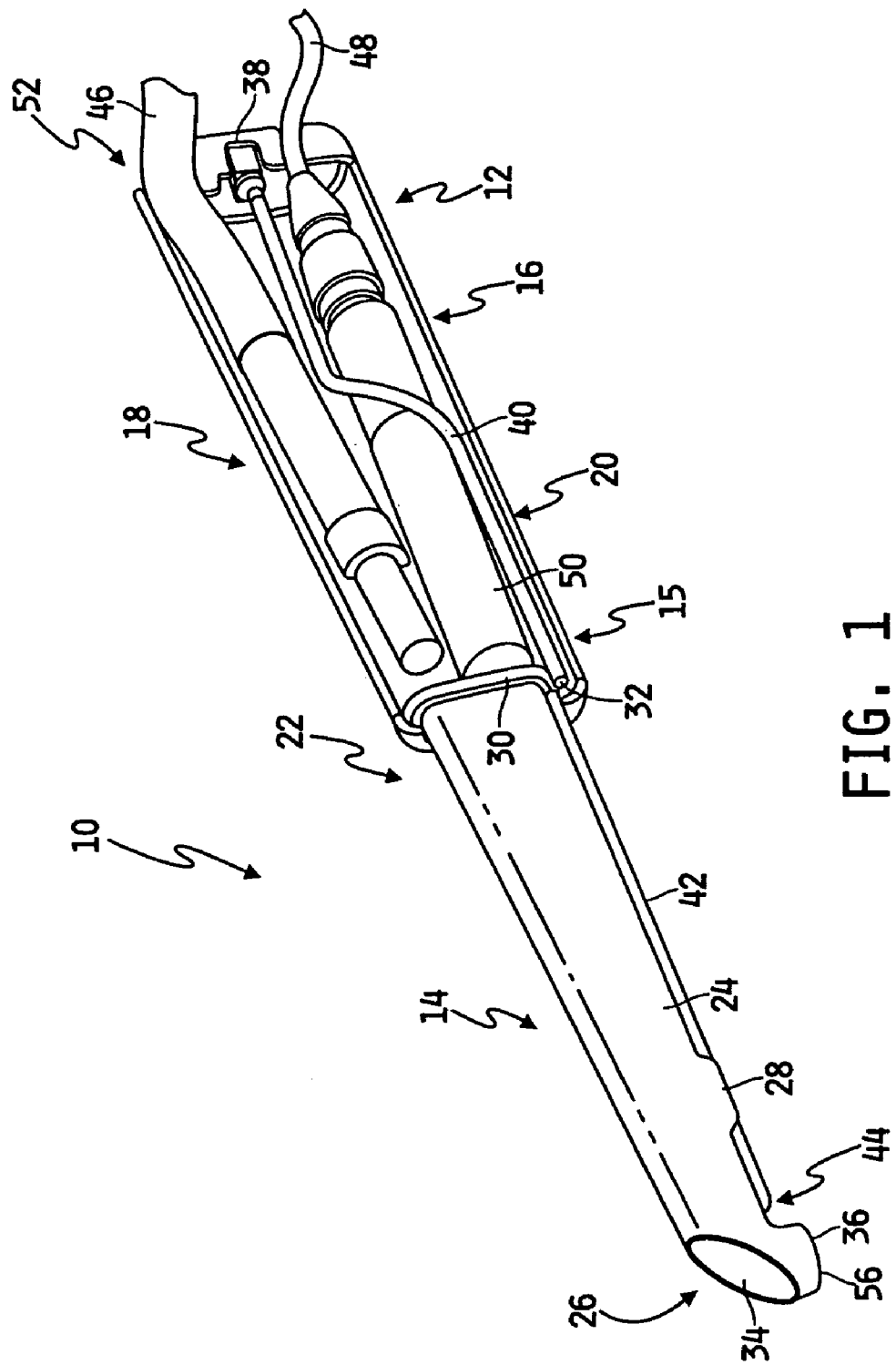
FIG. 1 is a perspective, partially cut-away view of a handpiece for dental caries detection.

To gather data for processing in a QLF system, a handpiece 10, shown in FIG. 1, is utilized. Handpiece 10 includes a handle or shell 12, a light pipe 14 attached to shell 12, an optical train 15 to receive light from light pipe 14, a camera 16 to detect light provided to optical train 15, a light source 18 to provide light to light pipe 14, and a conduit 20 extending through shell 12. Shell 12 includes a left half shell 21 and a right half shell 23 that cooperate to house, at least partially, optical train 15, camera 16, light source 18, and conduit 20. Shell 12 furthermore couples to light pipe 14 as shown in FIG. 1.

Shell 12 includes inner cavities shaped to receive and hold camera 16, light source 18, inter-shell hose 40, and light pipe 14 in specific orientations. Lip 30 of light pipe 14 is received in recess 32 of shell 12. Likewise, light source 18 is positioned to allow light therefrom to be directed through light pipe 14, off reflecting facet 34, and out inspection surface 36. Similarly, camera 16 is positioned such that light entering inspection surface 36, reflecting off reflecting facet 34, and traveling through light pipe 14 is received by camera 16. Additionally, shell 12 provides for wires (fiber optic, electrical, or otherwise) to extend from a rear end 52 thereof. A fiber optic cable 46 extends to the external light source (not shown), an electrical cable 48 extends to a computer (not shown) to store, process, and display the image received by camera 16.

Light source 18 is preferably a fiber optic system that conveys illumination from a remote source but may also be a local source within shell 12 or any other source known in the art. The light may be optically filtered by the system either before or after exiting light source 18. Such filtering excludes unwanted light and noise from the desired signal. Furthermore, in one embodiment, light source 18 includes one or more light emitting diodes, laser diodes, or some combination thereof (locally or remotely). In such embodiments, each of the light sources may be of a different wavelength and combined as desired. The wavelength of the light used may be tailored, lengthened or shortened, to the dental tissue being observed as well as to the desired light penetration and to the light collection instrumentation (camera 16) so as to provide the desired optical response. It should be appreciated that while much of the description herein refers to fluorescence as the desired optical response, all types of optical responses are intended to within the scope of the present disclosure. It should also be appreciated that the term "dental tissue" is used herein to include all types of tissue found in the mouth, i.e. teeth, gums, tongue, cancerous cells.

Optical train 15 includes a lens 50 and at least one filter. Embodiments are envisioned where lens 50 and the filter(s) may be combined into one structure or where no filter is present. Optical train 15 tailors the incoming information into a form that is best received by camera 16 and that best provides the data for processing. Such tailoring may include providing selective attenuation of the reflected or scattered input illumination, in addition to fluorescent emission data. While optical train 15 is described as having one lens 50 and filter, many lenses and filters may be included in optical train 15 to provide different fields of view and different magnifications.

Camera 16 is part of a digital imaging system that collects high-resolution images and live video of dental tissue. Camera 16 then transmits the images, either through a wire as shown or wirelessly, to a computer system for storage and processing. One such suitable model camera is the DXC-LS1/1 sold by Sony. In the present embodiment, camera 16 is a color camera that detects spectral responses of tissue to the provided illumination. However, in another embodiment, camera 16 is a black and white sensing camera. In one embodiment using black and white camera 16, a bandpass filter 15 configured to filter out light of substantially the same wavelength as the illumination source 18 is used and black and white camera 16 is used to detect scattering intensity. In another embodiment using black and white camera 16, a bandpass filter 15 configured to filter out light of substantially the same wavelength as the tissue fluorescence is used and black and white camera 16 detects the intensity of tissue fluorescence.

Before reaching camera 16, the light of the tooth images passes through light pipe 14. Light pipe 14 is a translucent (transparent) monolithic polymer such as polystyrene, polycarbonate, acrylic, or glass piece that attaches to an end of the shell 12. "Translucent" as used herein is meant to describe any material that is not opaque, thus meaning anything that transmits light while causing light diffusion as well as anything that is transparent (transmitting light without causing substantial light diffusion). While light pipe 14 is described and shown as being a solid piece, embodiments are envisioned having voids and gaps within light pipe 14. Light pipe 14 is constructed from polycarbonate but may be constructed from any material that will allow light transmission of an adequate fidelity and acceptable, preferably low, signal loss.

Figure 2:
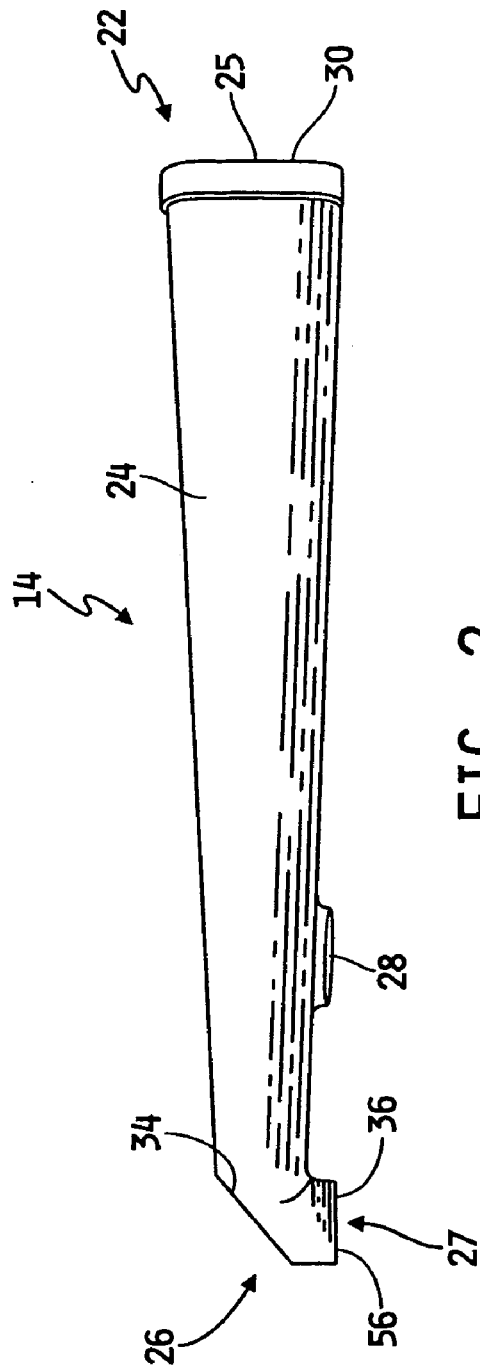
FIG. 2 is a perspective view of a lightpipe of the handpiece of FIG. 1.

As shown in FIG. 2, light pipe 14 includes a proximal attachment end 22, a tapering body 24, a distal end 26, and a conduit support 28. Proximal attachment end 22 includes a lip 30 of constant depth and width. Lip 30 is sized and shaped to be securely received in a recess 32 of shell 12. Separating left half shell 21 from right half shell 23 allows removal of light pipe 14. Coupling left half shell 21 to right half shell 23 secures light pipe 14 to shells 21, 23. Alternatively, shell 12 may be configured to have a pocket that slidably receives lip 30 therein and is secured by a latch so as to not require the detachment of left half shell 21 from right half shell 23.

Figure 3:
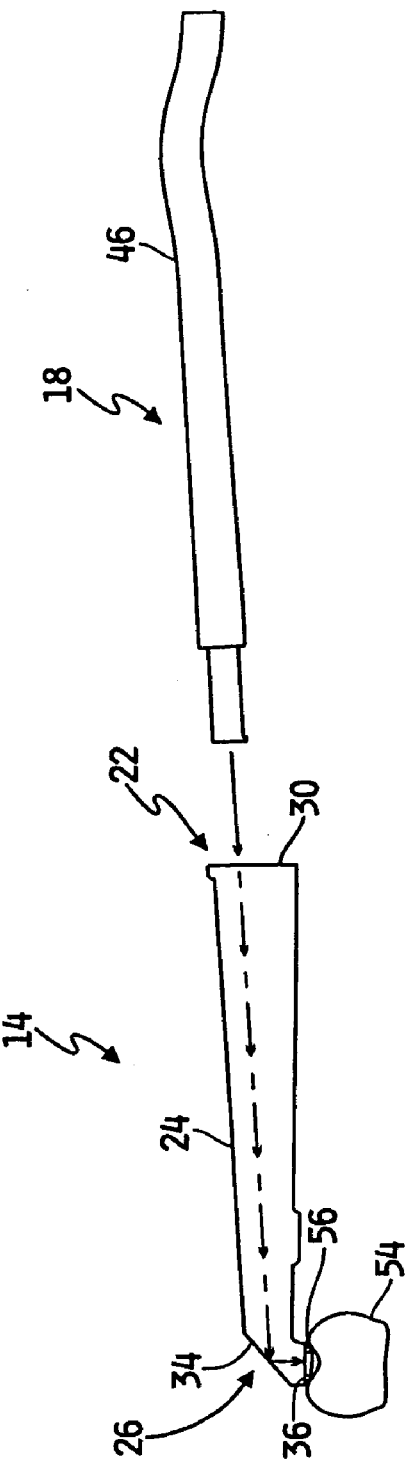
FIG. 3 is a cross sectional view of a light source and the lightpipe of FIG. 1 in contact with a tooth of a patient.
Figure 4:
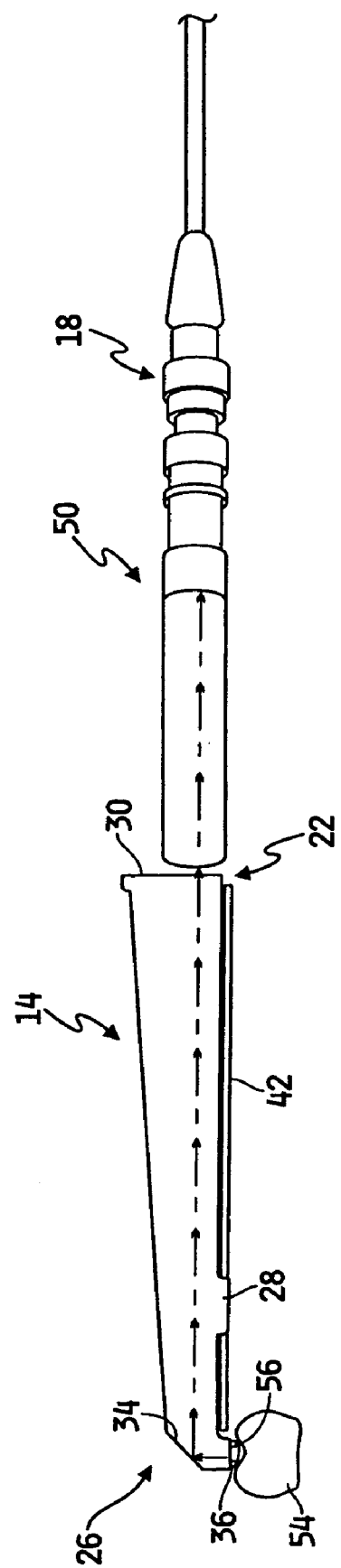
FIG. 4 is a side elevational view of a camera and the lightpipe of FIG. 1 in contact with a tooth of a patient.

Tapering body 24 includes conduit support 28 attached thereto which will be discussed in more detail below. Distal end 26 includes a reflecting facet 34 and an inspection surface 36. Reflecting facet 34 is in internal surface of light pipe 14. Reflecting facet 34 allows light entering from proximal attachment end 22 across a proximal light transfer plane 25 to reflect and exit through distal light transfer plane 27 of inspection surface 36 as shown in FIG. 3. Likewise, reflecting facet 34 allows light entering from distal light transfer plane 27 of inspection surface 36 to reflect and exit through proximal light transfer plane 25 of proximal attachment end 22 as shown in FIG. 4. As will be discussed in more detail later, reflecting facet 34 is shaped even more specifically to direct light from inspection surface 36 to camera 16. The reflective properties of reflecting facet 34 are provided by the difference in refractive index between the material of light pipe 14 and the air surrounding light pipe 14. Thus, it is not necessary to attach a reflective surface to light pipe 14 to achieve the reflecting properties of reflecting facet 34. However, embodiments are envisioned where an external member is attached to light pipe 14 to provide reflective properties.

Reflecting facet 34 is preferably at a 45-degree angle relative to inspection surface 36 and proximal attachment end 22. The 45-degree angle allows true image transmission and refraction between inspection surface 36 and proximal attachment end 22. However, it should be appreciated that embodiments are envisioned where reflecting facet 34 is not at a 45-degree angle, and various lenses, optical filters, and/or optical processors, either integral or external to light pipe 14, are utilized to construct a true image.

Tapering body 24 and distal end 26 are sized and shaped to be received in the mouth of a patient and to access posterior molars which, as a function of being farthest from the mouth opening, are typically the most difficult to access. Additionally, the size and shape of tapering body 24 allows the device to be used on smaller patients where oral space is more limited. Furthermore, light pipe 14 is lightweight, and as such provides increased maneuverability and less user fatigue.

Conduit 20 is provided to selectively deliver air to tooth 54 to dehydrate suspected lesions. Alternatively, conduit 20 may delivery any number of fluids to a position proximate distal end 26 of light pipe 14 such as a fluoride containing solution, other reparative fluids, a contrast agent, or a biomarker.

Conduit 20 extends within shell 12 and below tapering body 24. As shown in FIG. 1, conduit 20 includes a connector 38, an inter-shell hose 40, and an extra-shell channel 42. Connector 38 allows an external supply hose (not shown) to supply air, water, or another fluid to be attached to inter-shell hose 40. Inter-shell hose 40 is coupled to extra-shell channel 42 via shell 12 to allow matter from inter-shell hose 40 to pass into extra-shell channel 42 and out a distal end 44 of extra-shell channel 42. Extra-shell channel 42 is a metal channel that couples to conduit support 28 of light pipe 14 for support. Distal end 44 of extra-shell channel 42 is positioned such that any matter exiting therefrom will be proximate inspection surface 36. Such local delivery assists a caregiver in determining the activity status of a detected lesion.

To effect the delivery, a supply tube of air (not pictured) is attached to connector 38 and air is selectively pumped therethrough. Connector 38 is coupled to inter-shell hose 40 which is coupled to extra-shell channel 42 to allow localized delivery of the desired material. Furthermore, while the extra-shell channel 42 is shown as a tube that removably couples to an underside of light pipe 14, other embodiments include extra shell channel 42 defined within light pipe 14.

The shape and makeup of light pipe 14 are designed to create a focal plane 56 for camera 16 at or proximate to inspection surface 36. In use, inspection surface 36 is placed within a patient's mouth to abut a selected tooth 54. Abutting selected tooth 54, combined with the location of focal plane 56 of camera 16 allows for a caregiver to easily find a location for handpiece resulting in a clear picture. Focal plane 56 is configured to be at a distance that is the sum of the horizontal and vertical distances shown by dotted line in FIG. 4. Abutting inspection surface 36 with tooth 54 results in reproducibility of the desired picture from one inspection to the next by removing possible fluctuation of the distance between inspection surface 36 and tooth 54 between successive inspections and by reducing fluctuations from unsteadiness of an operator's hand. Light from light source 18, as it travels to and from tooth 54, only passes through ambient air for a short distance, if at all, when the inspection surface 36 abuts tooth 54. Control over the mediums through which the light passes increases the amount of control present over the signal and reduces chances for error that may be introduced if foreign matter is allowed in the light path. Furthermore, inspection surface 36 abutting tooth 54 increases the likelihood that only light provided by light source 18 is exciting the observed dental tissue and that the fluorescence observed by camera 16 is a result of the provided illumination rather than from ambient light. Inspection surface 36 abutting tooth 54 covers the portion of tooth 54 to be examined by the caregiver, thus light pipe 14 simultaneously provides desired illumination while not providing space between tooth 54 and handpiece 10 that would allow undesired tooth illumination.

It should also be appreciated that acrylic light pipe 14, or any plastic equivalent created by injection molding or otherwise, is relatively inexpensive to manufacture and thus may be used in a disposable fashion. Such disposable use results in increased hygiene practices for a dental practitioner. Non-disposable dental implements are typically subjected to a sterilization process, such as autoclaving, between patients. This sterilization is costly and can cause deterioration of the material being sterilized. Deterioration of a light pathway such as a lens, a mirror/reflecting surface, or a translucent material can adversely effect the pictures gathered from such equipment. Accordingly, the disposable nature of light pipe 14 results in increased image fidelity and increased hygiene for the patient. However, embodiments are also envisioned that incorporate a reusable light pipe 14.

When examining dental caries, active (growing) lesions, inactive lesions, and developmental defects are characterized by a localized decrease in mineralization. Defects are not typically repairable and inactive lesions often remain in such a state for years with no worsening of the condition. However, active lesions are growing decay that provide a heightened risk to the patient. Therefore, it is desirable to discriminate an active lesion from an inactive lesion or a tooth defect. Blowing air on the surface of tooth 54 containing the suspected lesion allows dehydration of the lesion and results in a change in the extent of the viewed damage image if the lesion is active. Non-active lesions and defects show no change in damage when dehydrated. Thus, it is desirable to be able to dehydrate lesions once found to determine their nature. It is furthermore desirable to be able to introduce a dehydration agent without gross alteration of camera 16 or the picture being taken so as to allow easy comparison of the hydrated and dehydrated pictures of the lesion.

In use, a dental care provider selects a handpiece 10 and attaches a lightpipe 14 (disposable or otherwise) thereto. Then, in certain embodiments, the provider places handpiece 10 within a sanitary sheath (not pictured) preferably made of thin plastic to provide a contaminant barrier for the entire handpiece 10. With or without the sheath, extra-shell channel 42 is then coupled to lightpipe 14 and intra-shell hose 40. The external light source and computer are activated to provide light to light source 18 and to receive data from camera 16. The provider then places distal end 26 of lightpipe 14 into the mouth of the patient such that inspection surface 36 of lightpipe 14 abuts chosen tooth 54.

If the patient has been examined with the system before, then the computer is instructed to bring up the previous tooth images. The provider, using a computer, attempts to match the placement of inspection surface 36 to the placement during the previous examination. The abutting of inspection surface 36 to tooth 54 removes one direction of motion that must be re-aligned to the previous examination. Once properly aligned, a picture is recorded and preferably saved to the computer. The provider then continues to perform this procedure on each tooth 54.

If, at any point, a suspected lesion is found, air may be introduced through conduit 20 to dehydrate the lesion and check the lesion for activity. A finding of an active lesion will permit the dental professional to implement a preventive treatment regimen consisting of periodic professional applications of a fluoride system, e.g., a fluoride varnish, and home-use of a daily fluoride treatment regimen. After a period of 2-3 months the lesion may be re-examined to determine the status and the need for further treatment regimens.

Figure 5:
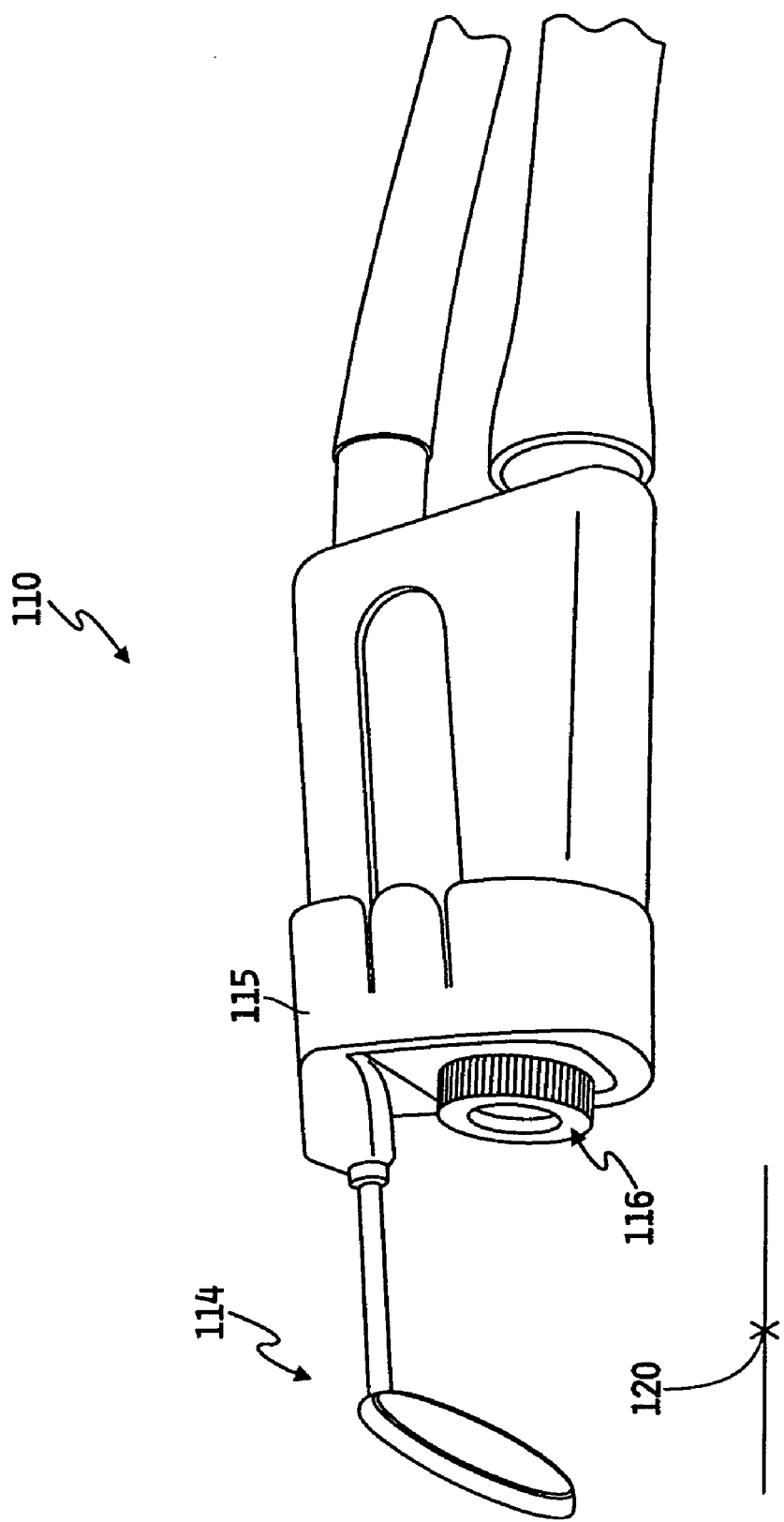
FIG. 5 is a perspective view of a prior art handpiece.

FIG. 5 shows a prior art handpiece 110 that is sold commercially by Inspektor. Inspektor handpiece 110 uses a detachable mirror 114 to aim light to tooth 54 and from tooth 54. Mirror 114 and mirror mount 115 detach such that mirror 114 and mirror mount 115 may be placed in an autoclave machine for purposes of sterilization. In use, Inspektor handpiece 110 is adjusted relative to tooth 54 such that the focal point 120 of a camera 116 is located on the tooth surface. Maintaining the focal point 120 of camera 116 on the tooth surface requires the provider to hold handpiece 110 steady. Proper placement of handpiece 110 is determined by using the received picture as feedback. In use, mirror 114 and a lens of camera 116 are open surfaces exposed to the oral environment. Thus, mirror 114 and lens of camera 116 are susceptible to collecting foreign debris.

Although the invention has been described in detail with reference to certain illustrated embodiments, variations exist within the scope and spirit of the invention as described and as defined in the following claims.

What is claimed is:

1. A method of detecting dental demineralization including the steps of:
   providing a handpiece including a light source, a light receiver, and a light conduit;
   abutting the light conduit to a crown of a selected tooth; and
   providing a stream of air via the handpiece to the tissue, the abutting step including positioning the light conduit in a first position abutting the tooth before the air providing step and further including the step of positioning the light conduit after the air providing step to substantially match the first position of the light conduit.

2. The method of claim 1, further including comparing an image received from the handpiece after the air providing step to a previously received image taken before the air providing step.

* * * * *